United States Patent [19]

Gibbs, Jr. et al.

[11] Patent Number: 4,977,517

[45] Date of Patent: Dec. 11, 1990

[54] LEAK AND CLOG DETECTION AND REMOVAL SYSTEM FOR USE WITH PARTICLE COUNTERS

[75] Inventors: Walden L. Gibbs, Jr., Wichita Falls; Jimmie L. Curry; William T. Mostyn, both of Hewitt, all of Tex.

[73] Assignee: Toni Diagnostics, Inc., Wichita Falls, Tex.

[21] Appl. No.: 247,411

[22] Filed: Sep. 21, 1988

[51] Int. Cl.$^5$ .................. G06G 7/57; G08B 21/00
[52] U.S. Cl. .................. 364/510; 364/555; 364/558; 377/21; 340/607; 340/608; 340/609; 340/611; 73/40.5 R; 128/DIG. 13
[58] Field of Search ............... 364/509, 510, 555, 558; 377/12, 21; 340/605, 607, 606, 608, 609, 611; 128/DIG. 12, DIG. 13; 73/40.5 R, 40

[56] References Cited

U.S. PATENT DOCUMENTS

| | | | |
|---|---|---|---|
| 3,699,319 | 10/1972 | Berg | 364/555 |
| 3,710,264 | 1/1973 | Doty et al. | 382/91 |
| 3,760,281 | 9/1973 | Hogg | 328/91 |
| 3,768,084 | 10/1973 | Haynes | 377/12 |
| 3,936,741 | 2/1976 | Coulter et al. | 324/71 C P |
| 3,938,038 | 2/1976 | Campbell | 324/71 C P |
| 3,987,391 | 10/1976 | Hogg | 324/71 C P |
| 4,072,934 | 2/1978 | Hiller et al. | 340/608 |
| 4,161,690 | 7/1979 | Feier | 324/71 C P |
| 4,165,484 | 8/1979 | Haynes | 377/12 |
| 4,167,038 | 9/1979 | Hennessy | 364/416 |
| 4,180,091 | 12/1979 | Hanley et al. | 324/71.4 |
| 4,198,855 | 4/1980 | Tsujikura | 73/40.5 |
| 4,218,610 | 8/1980 | Baxter, Jr. et al. | 377/12 |
| 4,240,029 | 12/1980 | Haynes | 377/12 |
| 4,309,757 | 1/1982 | Frey et al. | 364/555 |
| 4,314,346 | 2/1982 | Feier et al. | 364/555 |
| 4,384,971 | 5/1983 | Carter, II et al. | 252/106 |
| 4,412,175 | 10/1983 | Maynarez | 377/12 |
| 4,447,883 | 5/1984 | Farrell et al. | 364/555 |
| 4,488,248 | 12/1984 | Okada et al. | 364/555 |
| 4,555,662 | 11/1985 | Doutre et al. | 377/12 |
| 4,631,483 | 12/1986 | Proni et al. | 324/71.4 |
| 4,660,152 | 4/1987 | Downing et al. | 364/509 |
| 4,670,847 | 6/1987 | Furuse | 364/558 |
| 4,706,207 | 11/1987 | Hennessy et al. | 364/555 |
| 4,720,807 | 1/1988 | Ferran et al. | 364/509 |
| 4,751,501 | 6/1988 | Gut | 340/607 |
| 4,797,834 | 1/1989 | Honganen et al. | 364/510 |

Primary Examiner—Parshotam S. Lall
Assistant Examiner—Brian M. Mattson
Attorney, Agent, or Firm—Melvin A. Hunn

[57] ABSTRACT

In a particle counting system for sensing and counting particles, a sample fluid is drawn through an orifice from a sample chamber into a substantially enclosed fluid passage at a selected rate sufficient to maintain the pressure in the substantially closed fluid passage at a predetermined pressure level if the orifice and the substantially closed fluid passage are free from leaks and clogs. A sensor detects the actual pressure in the substantially closed fluid passage. The actual pressure is compared to the predetermined pressure level to identify clogs or leaks in the particle counting system. If a clog is identified, an automatic clog removal sequence is inititiated for dislodging or otherwise removing the clog from the particle counting system. The particle counting system is tested to determine if the clog has indeed been removed.

3 Claims, 4 Drawing Sheets

LEAK AND CLOG DETECTION AND REMOVAL SYSTEM FOR USE WITH PARTICLE COUNTERS

BACKGROUND OF THE INVENTION

1. Field of the Invention:

This invention relates generally to particle counting systems for sensing and counting particles suspended in a sample fluid as said sample fluid is drawn through an orifice from a sample chamber to a substantially enclosed fluid passage, and specifically to a system for detecting leaks and clogs in such particle counting system, automatically removing detected clogs, and automatically testing to verify that the detected clogs have been removed.

2. Description of the Prior Art:

Particle counting systems are widely used for sensing and counting particles suspended in a sample fluid as the sample fluid is drawn through a tiny orifice from a sample chamber into a substantially enclosed fluid passage. In the medical field, particle counting systems are used to count both red and white blood cells. An electrode is placed on each side of the tiny orifice, and a constant DC current is directed through the orifice via the sample fluid. Red and white blood cells obstruct the DC current path as they pass through the orifice. The blood cells physical obstruction of the current path through the orifice results in a voltage pulse between the electrodes as blood cells are caused to pass through the orifice by hydraulic pressure. By counting the voltage pulses, one may indirectly count the number of blood cells passed through the orifice.

It is important to recognize that blood cell and other counts are only meaningful if they can accurately reflect the number of cells or particles per volumetric unit. Therefore, it is critical that a particle counting system be adapted to pass a selected amount of sample fluid through the orifice as desired—no more, no less. Leaks or clogs in the particle counting system will result n either under-counting or over-counting of blood cells or particles per unit volume.

It is widely known that organic sample fluids such as blood tend to coagulate or accumulate upon the surfaces with which it comes into contact. For example, in the blood cell counters, blood and other organic materials tend to accumulate at the orifice, or along the internal periphery of the fluid passages in a particle counting system Such accumulations often result in clogs which impair or impede the passage of sample fluids through the system, resulting in gross miscalculations of particles per unit volume.

Disconnected tubes, faulty seals, and physical breaches in fluid passages can result in leakages that also undermine the accuracy of a particle count. Such leakages are common problems in particle counting systems, and are particularly harmful when small enough to remain substantially undetectable.

If undetected, clogs and leaks can result in numerous harmful errors, particularly in the field of medical diagnostics, where such errors can pose serious health and safety risks to patients, since doctors and other medical personnel rely heavily upon the results of blood cell and other counts in making a medical diagnosis, prescribing medication, and formulating medical strategies for the treatment of all types of injuries and diseases.

SUMMARY OF THE INVENTION

The present invention is a system for detecting clogs and leaks in a particle counting system, and for automatically removing detected clogs, and testing the particle counting system to verify that the clogs have been removed.

It is one object the present invention to provide a leak and clog detection system which detects leaks or clogs anywhere in the main fluid circuit.

It is another object of the present invention to allow for continuous and automatic leak and clog detection in a particle counting system.

It is yet another object of the present invention to provide a means for automatically removing clogs when detected and for verifying that the clog has been removed.

The foregoing objects are achieved as is now described. In a particle counting system for sensing and counting particles, a sample fluid is drawn through an orifice from a sample chamber into a substantially enclosed fluid passage at a selected rate sufficient to maintain the pressure in the substantially enclosed fluid passage at a predetermined pressure level if the orifice and the substantially enclosed fluid passage are free from leaks and clogs. A sensor means detects the actual pressure in the substantially enclosed fluid passage. The actual pressure is compared to the predetermined pressure level to identify clogs or leaks in the particle counting system. If a clog is identified, an automatic clog removal sequence is initiated for dislodging, dissolving, or otherwise removing the clog from the particle counting system. Then the particle counting system is tested to determine if the clog has indeed been removed.

The above as well as additional objects, features, and advantages of the invention will become apparent in the following detailed description.

BRIEF DESCRIPTION OF THE DRAWING

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE INVENTION

Figure 1:
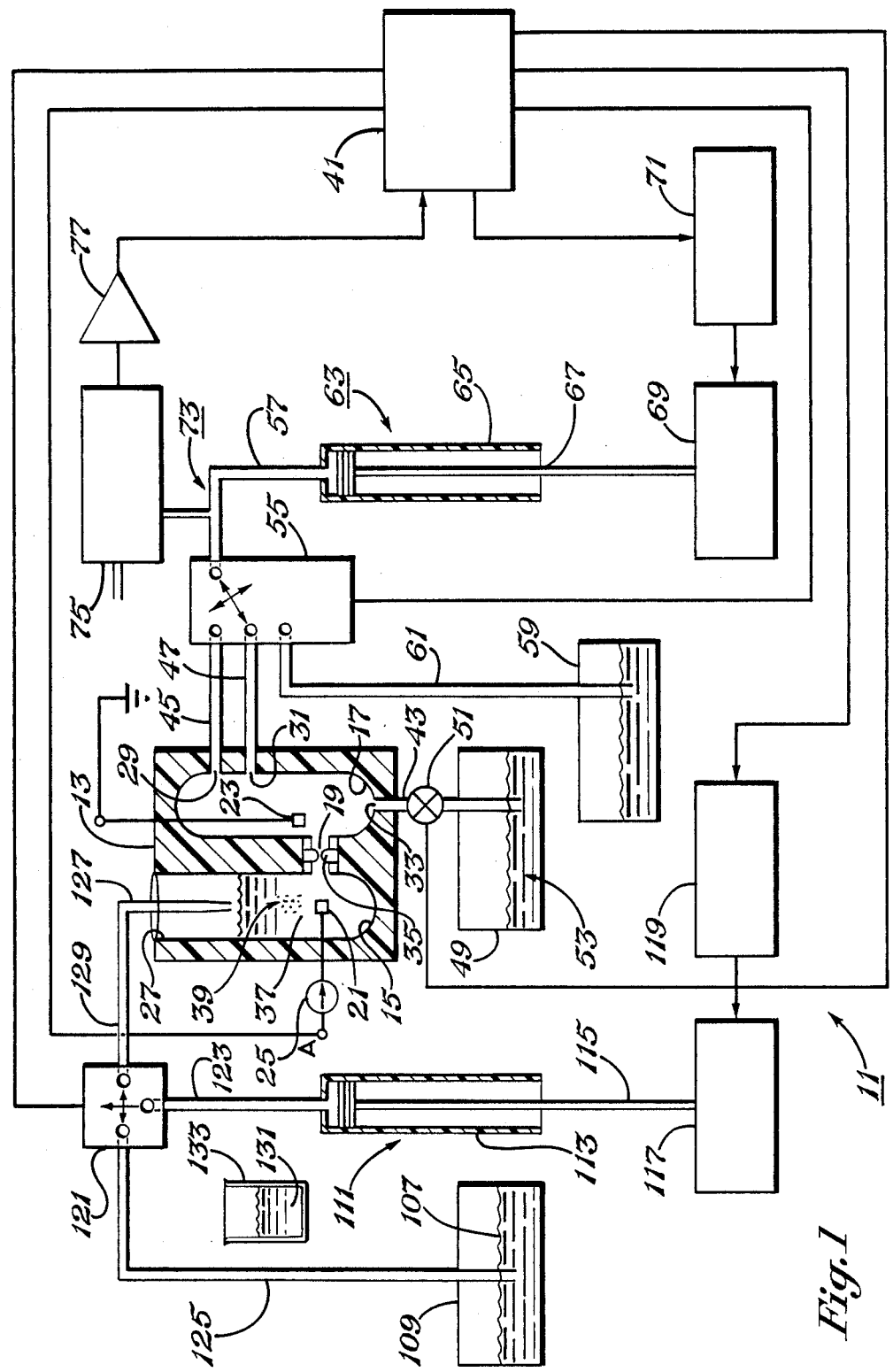
FIG. 1 is a block diagram of a particle counting system having a leak and clog detection, and clog removal capabilities according to the present invention.

With reference now to the figures and in particular with reference to FIG. 1, the improved particle counting system of the present invention is now described. In particle counting system 11, sample chamber 15 and draW chamber 17 are coupled by orifice 19, which allows for the passage of fluid from sample chamber 15 to draw chamber 17. In the preferred embodiment, sample chamber 15 and draw chamber 17 are formed from a single piece of durable, transparent material identified as cell 13. Sample chamber 15 is quite small, having a volume of approximately two and one half milliliters in the preferred embodiment. Likewise, orifice 19 is also quite small, having a diameter of approximately 100 microns which allows for the passage of only small amounts of fluid from sample chamber 15 to draw chamber 17. In the preferred embodiment, orifice 19 is formed in jewel 35, which is a synthetic sapphire. Sample chamber 15 is open to the environment at sample port 27, serving to allow for the delivery of sample fluids and other fluids into sample chamber 15. Draw chamber 17 has three tiny ports for coupling draw chamber 17 to a fluidic circuit: rinse draw port 29, sample draw port 31, and rinse reservoir port 33.

Two electrodes are disposed in cell 13, one in sample chamber 15, and the other in draw chamber 17. More specifically, electrode 21 is disposed in sample chamber 15 on one side of orifice 19. Electrode 23 is disposed in draw chamber 17 on the opposite side of orifice 19. Constant current source 25 is electrically coupled to electrode 21, and serves to pass a constant level current from sample chamber 15 through orifice 19 to draw chamber 17 via sample fluid 37 which is an electrolytic fluid capable of conducting currents. As particles 39 suspended in sample fluid 37 are drawn through orifice 19 they physically obstruct the current path and produce a voltage pulse measurable between electrodes 21, 23. The operation of constant current source 25 is controlled by computer 41 which is electrically coupled to constant current source 25 at terminal A. In addition, computer 41 serves to detect and count voltage pulses generated by the passage of particles 39 through orifice 19.

As stated above, draw chamber 17 is coupled to a fluid circuit via rinse draw port 29, sample draw port 31, and rinse reservoir port 33. Rinse reservoir 49 is coupled to rinse draw port 29 via rinse reservoir line 43. Rinse valve 51 is disposed in rinse reservoir line 43, and is electrically coupled to computer 41. Computer 41 controls the operation of rinse valve 51 to allow or prevent the passage of rinse fluids 53 from rinse reservoir 49 to draw chamber 17.

Draw chamber 17 is coupled to rotary valve 55 by rinse draw line 47 at rinse draw port 29, and by sample draw line 47 at sample draw port 31. Rotary valve 55 is in turn connected to pump line 57, and waste reservoir via waste line 61. Rotary valve 55 is electrically operated and controlled by computer 41, and serves to selectively couple pump line 57 to rinse draw line 45, sample draw line 47, or waste line 61, as is shown schematically in FIG. 1. Rotary valve 55 allows for only one connection. Therefore pump line 57 may not be simultaneously connected to more than one other line; however, rotary valves 55 allows for the consecutive connection and reconnection of pump line 57 to rinse draw line 45, sample draw line 47, and waste line 61.

In the preferred embodiment, pump line 51 is coupled to a positive displacement pump such as pump syringe 63. Pump syringe 63 consists of syringe cylinder 65 having a syringe plunger 67 disposed therein and moveable relative to syringe cylinder 65. The advancement and retraction of syringe plunger 67 relative to syringe cylinder 65 is accomplished by drive mechanism 69 which is controlled by computer 41 through drive controller 71.

The fluidic passage described above from orifice 19 through pump syringe 67 is a substantially closed system, with the exception of orifice 19. For purposes of exposition, this fluid passage may be identified as substantially enclosed fluid passage 73. As syringe plunger 67 is retracted within syringe cylinder 65, a vacuum is developed in substantially enclosed fluid passage 73, which draws sample fluid 37 from sample chamber 15 into substantially enclosed fluid passage 73. The strength of the vacuum developed by pump syringe 63 will determine, in-part, the rate of flow of sample fluid 37 through orifice 19. If a count of particles 39 in sample fluid 37 is desired, rotary valve 55 is actuated to couple sample draw line 47 to pump line 57. Therefore, as syringe plunger 67 is retracted within syringe cylinder 65, sample fluid 37 is drawn from sample chamber 15 through orifice 19 into draw chamber 17. As sample fluid 37 passes through orifice 19, particles 39 suspended therein are counted. Sample fluid 37 thereafter exits draw chamber 17 through sample draw port 31 into sample draw line 47, through rotary valve 55 and into pump line 57. Sample fluid 37 is drawn from pump line 57 into syringe cylinder 65 as syringe plunger 67 is retracted by drive mechanism 69. After a predetermined quantity of sample fluid 37 has been drawn through orifice 37, rotary valve 55 is switched to couple pump line 57 to waste line 61, and syringe plunger 67 is advanced within syringe cylinder 65 of pump syringe 63 to exhaust sample fluid 37 from syringe cylinder 65 into waste reservoir 59.

The residue of sample fluid 37 remaining in substantially enclosed fluid passage 73 may be removed by rinsing substantially enclosed fluid passage 73 with rinse fluid 53 from rinse reservoir 49. When a rinse is desired, computer 41 simultaneously actuates rinse valve 51 to allow the flow of rinse fluid 53 from rinse reservoir 49 into draw chamber 17 via rinse reservoir line 43, and rotary valve 51 to couple pump line 57 to rinse draw line 45. Then, computer 41 actuates drive mechanism 69 through drive controller 71 to retract syringe plunger 67 within syringe cylinder 65 to draw rinse fluid 63 from rinse reservoir 49 into draw chamber 17. Rinse fluid 53 then passes from draw chamber 17 through sample draw line 47, through rotary valve 55 and pump line 57 into syringe cylinder 65. Thereafter, computer 41 actuates rotary valve 55 to couple pump line 57 to waste line 61, and actuates drive mechanism 69 through drive controller 71 to advance syringe plunger 67 within syringe cylinder 65 to exhaust rinse fluid 53 from syringe cylinder 65 into waste reservoir 59.

In the present invention, a means is provided for determining whether leaks or clogs exist in substantially enclosed fluid passage 73. As discussed above, leaks and clogs result in unacceptable particle counting errors. In the preferred embodiment, pressure sensor 75 is coupled to pump line 57, and serves to detect pressure within substantially enclosed fluid passage 73 as sample fluid 37 is drawn from sample chamber 15 through orifice 19. Pressure sensor 75 serves to provide a general measure of the pressure differential created across orifice 19 in sample fluid 37 as pump syringe 63 attempts to produce a vacuum in substantially enclosed fluid passage 73. In the preferred embodiment, pressure sensor 75 provides a measure of the pressure differential between substantially enclosed fluid passage 73 and atmosphere. Also in the preferred embodiment, pressure sensor 75 is a MICROSWITCH brand pressure transducer, Model Number 16PC15GF. The signal produced by pressure sensor 75 is amplified by amplifier 77, which in the preferred embodiment is a VURR-BROWN brand precision instrumentation amplifier, Model Number 1NA101. The amplified signal is directed to computer 41.

Figure 2:
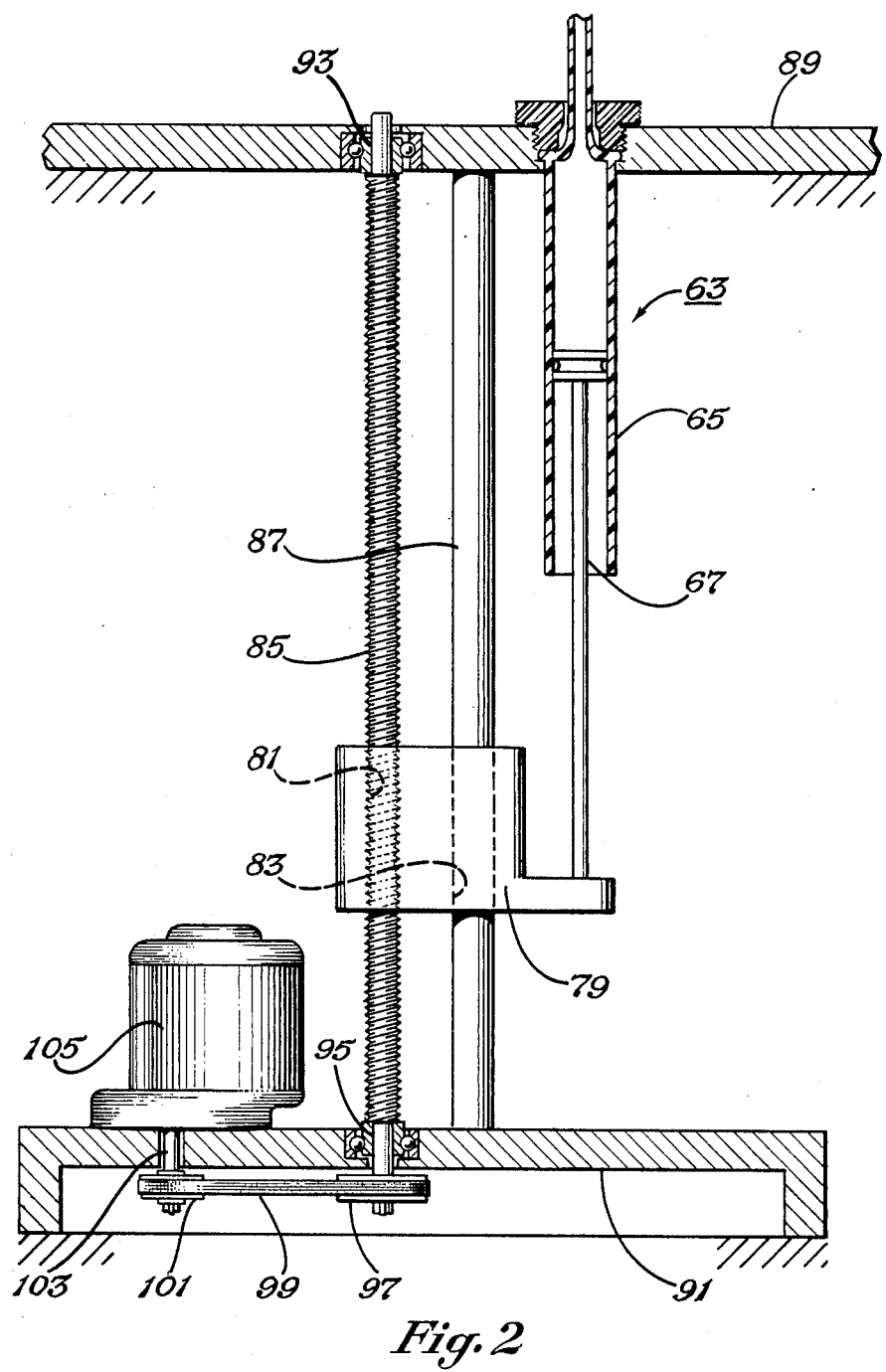
FIG. 2 is a perspective view of the drive mechanism of the present invention.

In FIG. 2, the drive mechanism 69 of the present invention is depicted in perspective view. Basically, the drive mechanism consists of a traveling block 79 which is coupled to syringe plunger 67 of pump syringe 63. Traveling block 79 has two parallel bores disposed therein. Worm bore sI is adapted to receive worm drive 85, while sliding bore 83 is adapted to receive rod 87. Rod 87 is non-rotatably secured between parallel top plate 89 and bottom plate 91. In contrast, worm drive 85 is a helically threaded rod that is rotatable carried between top plate 89 and bottom plate 91 at upper bore and lower bore 95. Pulley 97 is concentrically disposed about the lower end of worm drive 85. It is coupled by rubber belt 99 to shaft pulley 101 which is concentrically disposed about shaft 103 of DC stepper motor 105. In the preferred embodiment, DC stepper motor 105 comprises a HOWARD brand unipolor stepping motor. The drive controller 71 of FIG. 1 is merely a conventional switching circuit commonly used with stepper motors to allow for forward and reverse movement of the DC stepper motor 105 in either full or one-half "steps". Stepper motor "steps" are defined as 1.8° of rotation of shaft 103. Consequently, one half steps are defined as 0.9° of rotation The HOWARD DC stepper motor 105 of the present invention allows four types of control over the stepper motor including turning the motor on and off, and advancing or retracting the stepper motor either one-half step or one full step.

In operation, rotation of the DC stepper motor 105 will rotate worm drive 85 in one direction, causing traveling block 79 to slide upward along rod 87. This causes syringe plunger 67 to be urged inward along syringe cylinder 65, pushing fluid from pump syringe 63. In contrast, when DC stepper motor 105 is rotated in the opposite direction, worm drive 85 is caused to rotate in the opposite direction, lowering traveling block 81 relative to top plate 89. When this occurs, syringe plunger 67 is retracted within syringe cylinder 65, drawing fluid into pump syringe 63. The present drive mechanism 69 allows for highly accurately controlled displacement and movement of fluids within substantially enclosed fluid passage 73.

Returning now to FIG. 1, it is often desirable to introduce other types of fluids into the particle counting system of the present invention. For example, it may be desirable to provide a diluent fluid 107 from diluent reservoir 109 into sample chamber 15. This is accomplished by operation of diluent syringe 111, which consists of diluent syringe cylinder 113 having diluent syringe plunger 115 disposed therein. Like pump syringe 63, diluent syringe plunger 115 is advanced and retracted within diluent syringe cylinder 113 by drive mechanism 117 and drive controller 119. Of course, computer 41 controls diluent syringe 111 through drive mechanism 117 and drive controller 119. Drive mechanism 119 is identical to drive mechanism 69.

Diluent syringe 111 is coupled to diluent rotary valve 121 via syringe line 123. Diluent rotary valve 121 serves to selectively couple diluent syringe 111 to either diluent reservoir 109 through diluent reservoir line 125, or through nozzle 127 via nozzle line 129. Nozzle 127 is adjustable relative to sample port 127 of sample chamber 15, and may serve to dispense diluent 107 into sample chamber 15 when desired. Rotary valve 121 is controlled and operated by computer 41.

In operation, when diluent is desired in sample chamber 15, computer 41 switches diluent rotary valve 121 to couple diluent syringe 111 to diluent reservoir 109. Then computer 41 actuates drive mechanism 117 through drive controller 119 to retract diluent syringe plunger 115 within diluent syringe cylinder 113, pulling diluent 107 into diluent syringe cylinder 113. Then, computer 41 switches diluent rotary valve 121 to couple diluent syringe 111 to nozzle line 129. Thereafter, computer 41 causes drive mechanism 117 to advance diluent syringe plunger 115 within diluent syringe cylinder 113 to exhaust diluent 107 through nozzle line 129 into nozzle 127 for dispensation into sample chamber 15.

METHOD OF DETECTING LEAKS AND CLOGS

The above described particle counting system 11 may be used to detect leaks and clogs present in a substantially enclosed fluid passage 73 which would, if undetected, impair the accuracy of the particle count. In order to accurately detect leaks and clogs, sample fluid 37 must be drawn through the particle counting system 11 at a highly controlled, uniform rate, which is sufficient to maintain said substantially enclosed fluid passage 73 at a predetermined constant pressure level.

The relationship between the uniform rate at which sample fluid 37 is drawn through substantially enclosed fluid passage 73 and the constant pressure differential developed between substantially enclosed fluid passage 73 and atmosphere depends, of course, upon the physical and fluidic characteristics of each particle counting system 11. Therefore, the pressure differential developed at a particular rate of retraction of pump syringe 63 must be established empirically. Pressure measurements are made on a system when it is known to be free from leaks and clogs. The information provided from such measurements may be programmed into computer 41 memory and compared to the actual pressure sensed by pressure sensor 75 when pump syringe 63 is actuated at an identical rate. The pressure expected from such rate is referred to hereinafter as the "predetermined pressure level."

In the preferred embodiment, for example, if syringe plunger 67 in retracted at 75.5 steps per second, a vacuum of six inches of mercury is developed in substantially enclosed fluid passage 73. This amounts to a pressure differential of approximately three pounds per square inch within substantially enclosed fluid passage 73. Since it has been empirically determined that retraction of syringe plunger 67 at 75.5 steps per second produces a predetermined pressure level of three pounds per square inch within substantially enclosed fluid passage when said substantially enclosed fluid passage 73 and orifice 19 are free from leaks and clogs, subsequent particle counts in which sample fluid 37 is drawn at an identical rate should produce an identical pressure within substantially enclosed fluid passage. If, however, a clog exists in the system, pressure sensed by pressure sensor 75 will be substantially greater than three pounds per square inch. In contrast, if a leak exists in substantially enclosed fluid passage 73, the pressure developed within substantially enclosed fluid passage 73 by retraction of syringe plunger 67 at the uniform preselected rate, will result in an actual pressure of less than three pounds per square inch within substantially enclosed fluid passage 73.

Additionally, it is preferable to provide for a range of preselected acceptable pressure levels between an upper acceptable pressure above the predetermined pressure level and a lower acceptable pressure below the predetermined pressure level. This allows a modest margin of acceptable error, and minimizing the occurrence of false indications of leaks and clogs.

Problems where encountered in achieving a constant pressure level within substantially enclosed fluid passage 73 within a sufficiently short period of time. The solution of this problem was to "ramp-up" the system in a very short time interval. This process requires the retraction of syringe plunger 67 at a rate significantly higher than the ordinary driving rate for the testing of samples. For example, in the preferred embodiment, the ramp-up rate is approximately 300 steps per second, compared to the operating rate of approximately 75 steps per second. Again, of course, these rates will vary with the particulars of each system. The object of driving the syringe plunger 67 at such a rapid rate is to overcome the ordinarily slow response of the fluid system due to its critically-damped nature.

Figure 3:
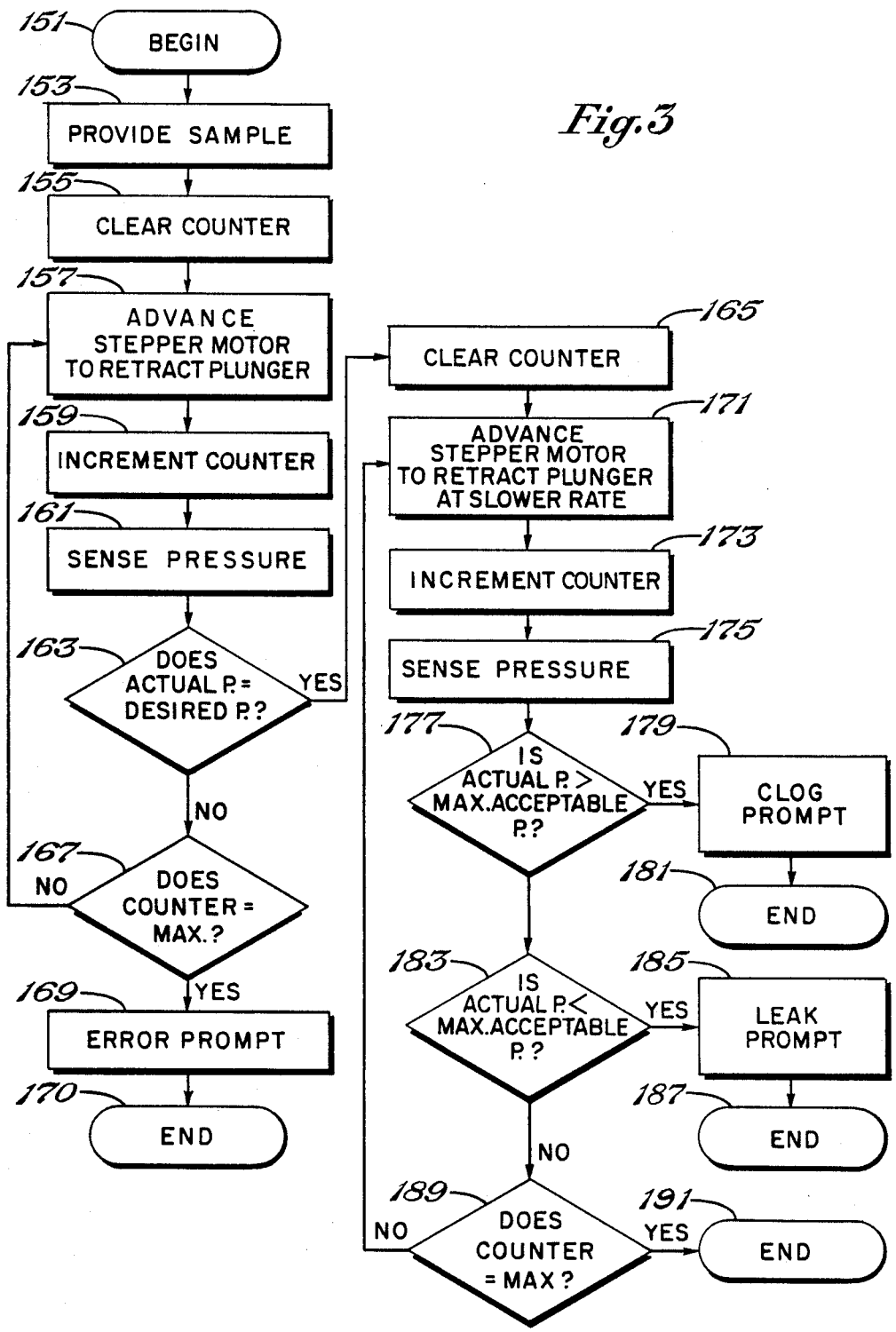
FIG. 3 is a flowchart of the leak and clog detection system of the present invention.

Turning now to FIG. 3, the method steps of the present invention are depicted in flowchart form. At step 151, the process begins. In step 153, sample fluid 37 with suspended particles 39 therein is provided in sample chamber 15 for analysis. Next, a counter in computer 41 memory is cleared in step 155. Then, in step 157, computer 41 actuates pump syringe 63 through drive controller 71 and drive mechanism 69 to retract syringe plunger 67 from syringe cylinder 65 at a very rapid rate.

After each step of DC stepper motor 105, the counter is incremented in step 159, and the pressure in substantially enclosed fluid passage 73 is sensed by pressure sensor 75 in step 161. The pressure sensed in step 161 is then compared by computer 41 to a predetermined pressure level in computer memory, in step 163. If the actual pressure is equal to the predetermined pressure level, the counter is cleared in step 165. If not, the value of the counter is compared to a preselected number of steps allowed in the ramp-up in step 167. If the value of the counter equals the maximum number of steps allowed, an error is indicated in step 169. The maximum number of steps allowed is selected to allow the system to achieved the predetermined pressure level. If this pressure level cannot be obtained in a certain number of steps, a large systemic error has been detected, such as a disconnected hose. In other words, if the desired pressure cannot be reached within a given number of steps, an enormous leak exists in the system. If, however, in step 167 the counter value does not equal to the maximum, the process returns to step 157 for iteration.

However, when the desired pressure is eventually achieved in step 163, and the counter is cleared in step 165, and the process of drawing the sample to orifice 19 into substantially enclosed fluid passage 73 begins. At step 171, DC stepper motor 105 is activated to retract syringe plunger 67 one step (at a lower rate than during ramp-up). Then in step 173, the counter in incremented to account for the step made in step 171. At step 175, pressure sensor 75 senses the actual pressure in substantially enclosed fluid passage 73. Then, in step 177, the actual pressure sensed is compared to the maximum acceptable pressure level stored in computer 41 memory. If the actual pressure level exceeds such maximum acceptable pressure level, a clog has been detected, and in step 179, a clog prompt is provided at computer 41, and the particle counting process is discontinued in step 181.

If in step 177 the actual pressure does not exceed the maximum acceptable pressure, then the actual pressure is compared to the minimum acceptable pressure in step 183. If the actual pressure is less than the minimum acceptable pressure, a leak prompt is provided in step 185 at computer 41, and the particle counting process ends at step 187. If, hoWever, the actual pressure is determined to be greater than the minimum acceptable pressure in step 183, at step 189, the value of the counter is compared to a predetermined maximum stored in computer 41 memory. If the maximum number of steps has been achieved in step 189, the process ends at step 191, indicating that a complete sample has been drawn and the particle counting process is complete. If, however, the counter does not equal the maximum, then the process returns to step 171 where the DC stepper motor is advanced an additional step to retract syringe plunger 67 further. This loop is continued until either a clog is detected, a leak is detected, or the particle counting process is completed.

CLOG REMOVAL METHOD

In the preferred embodiment of the present invention, when a clog is detected the particle counting system 11 commences a sequence of procedures aimed at removing the clog from the system. Such procedures are interspersed with testing to determine if the clog has been removed by the previous procedure.

Figure 4:
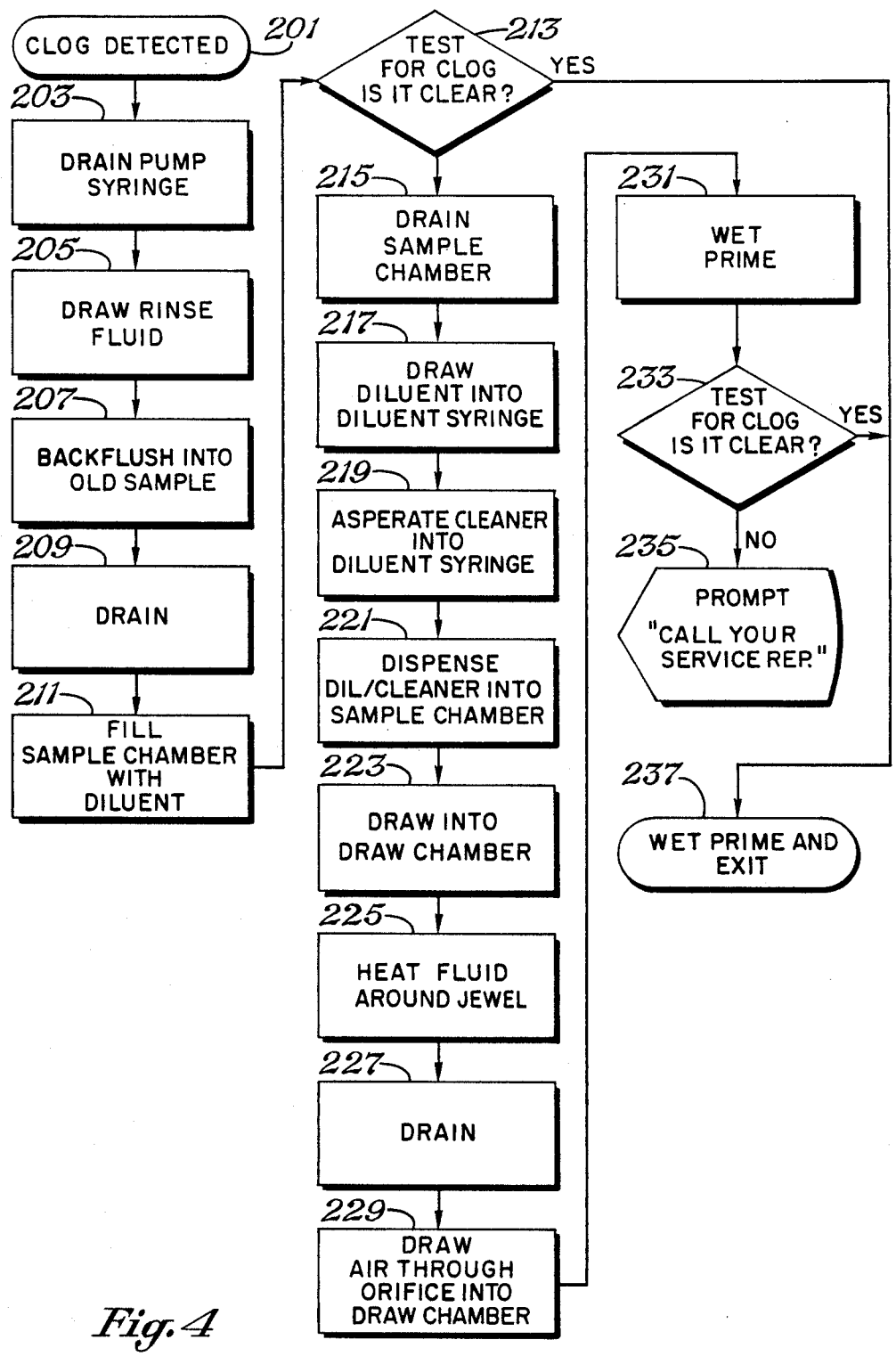
FIG. 4 is a flowchart of the clog removal system of the present invention.

Turning now to FIG. 4, the preferred method is depicted in flowchart form. At step 201 the process begins when a clog is detected. In step 203, computer 41 activates rotary valve 55 and pump syringe 63 to drain pump syringe 63 into waste reservoir 59. Next, in step 205, computer 41 actuates rotary valve 55, rinse valve 51 and pump syringe 63 to draw rinse fluid 53 from rinse reservoir 49 into substantially enclosed fluid passage 73.

Next, in step 207, computer 41 actuates pump syringe 63 to flush rinse fluid 53 backward through substantially enclosed fluid passage 73, through orifice 19, and into sample chamber 15, where it mixes with the unused sample fluid 37. Then, computer 41 actuates pump syringe 63, rotary valve 55, to draw this mixture of sample fluid 37 and rinse fluid $3 inward to syringe cylinder 65, and then back through pump line 57 and rotary valve 55 to waste reservoir 59.

In step 211, sample chamber 15 is filled with diluent. More specifically, computer 41 actuates diluent syringe 111, and diluent rotary valve 121 to draw diluent fluid 107 from diluent reservoir 109. Then, computer 41 switches diluent rotary valve 121 to allow diluent syringe 111 to expel diluent fluid 107 from diluent syringe cylinder 113 through nozzle line 129, and nozzle 127 into sample chamber 15.

At step 213, computer 41 tests particle counting system 11 to determine if the previously detected clog has been removed. Of course, the method of testing is identical to the method employed in detecting the clog. More specifically, diluent fluid 107 is advanced through orifice 19 by action of pump syringe 63. At each step of DC stepper motor 105, computer 41 compares the actual pressure sensed by pressure sensor 75 to the predetermined pressure level in computer 41 memory, which corresponds to the expected pressure during normal operation of particle counting system 11. If particle counting system 11 is indeed free of clogs, the particle counting system is "wet primed" and computer 41 exits the clog removal subroutine at step 237. The term "wet prime" refers to the process of returning particle counting system 11 to a condition for the receipt of a new sample for analysis.

If in step 213 the test reveals that the clog has not been removed, in step 215, computer 41 actuates pump syringe 63 and rotary valve 55 to drain sample chamber 15. Then, in step 217, computer 41 causes diluent syringe 111 to draw diluent into diluent syringe cylinder 113.

Next, in step 219, the operator is instructed to place nozzle 127 in a container 133 of cleaning fluid 131, and the cleaning fluid 131 is aspirated upward through nozzle 127 into diluent syringe cylinder 113 where it is mixed with diluent fluid 107. In step 221, computer 41 causes diluent syringe 111 to dispense the mixture of diluent fluid 107 and cleaning fluid 131 into sample chamber 15.

In step 223, computer 41 causes pump syringe 63 to draw this mixture of fluids into draw chamber 17. In step computer 41 activates constant current source 25 for a relatively prolonged period of time (in the preferred embodiment, approximately ten seconds), heating the mixture of fluids in the vicinity of jewel 35, and especially in the vicinity of orifice 19. This heating aids in dislodging clogs. In step 227, all fluid is drained from substantially enclosed fluid passage 73, as well as sample chamber 15. In step 229, pump syringe 63 is caused by computer 41 to draw air through orifice 19 into draw chamber 17. The system is wet primed in step 231 and retested for the presence of clogs in step 233. If the clog has been removed, the process continues at step 237 where the particle counting system is wet primed again and the subroutine is exited. If, however, the clog has not been removed, the computer prompts the operator to call a service representative, since the clog is probably not removable through the automated clog removal process.

The clog removal process described above consists of a procedure whereby fluid is flushed backwards through the system in an attempt to dislodge clogs. Then, a solution containing a cleaning fluid is introduced into the particle counting system 11 in an attempt to dissolve or chemically remove the clog from the system. This cleansing process may be coupled with heating, with under certain circumstances improves the dissolution of clogs. Of course, as described, the particle counting system 11 may be tested at one or more of these stages to determine if the clog has been removed by the subsequent procedure.

The present invention presents a variety of advantages over prior art systems. First, the leak and clog detection system of the present invention allows one to detect leaks and clogs that occur anywhere in the main fluid circuit of a particle sensing and counting apparatus. Second, the present system is adapted to detect both leaks and clogs avoiding the duplication of equipment, and resulting in savings. Third, the system allows for a continuous and automatic detection of leaks and clogs. The system is certainly more accurate than prior art systems since it will detect protein buildup or small leaks at very early stages, that would ordinarily go unnoticed by an operator. Gradual buildups of blood protein on tubing, valves, and orifices can be detected. Fourth, the system presents a means for automatically removing clogs once detected. Fifth, the leak and clog detection system of the present invention allows the leak and clog tolerance levels to be selected by the operator to suit the particular testing needs.

Although the invention has been described with reference to a specific embodiment, this description is not meant to be construed in a limiting sense. Various modifications of the disclosed embodiment as well as alternative embodiments of the invention will become apparent to persons skilled in the art upon reference to the description of the invention. It is, therefore, contemplated that the appended claims will cover any such modifications or embodiments that fall within the true scope of the invention.

What is claimed is:

1. A method of detecting a clog in a particle counting system for sensing and counting particles suspended in a sample fluid as said sample fluid is drawn through an orifice from a sample chamber to an enclosed fluid passage, comprising:

advancing said sample fluid from said sample chamber through said orifice to said enclosed fluid passage at a selected rate to maintain said enclosed fluid passage at a predetermined pressure level if said particle counting system is clog-free;

sensing and counting said particles suspended in said sample fluid as said sample fluid is drawn through said orifice from said sample chamber to said enclosed fluid passage;

sensing actual pressure in said enclosed fluid passage as said sample fluid is advanced through said orifice;

comparing said actual pressure to said predetermined pressure level;

identifying the clog in said particle counting system when said actual pressure exceeds said predetermined pressure level;

providing a cleaning fluid for removing said clog in said particle counting system;

automatically pumping said cleaning fluid through said orifice and said enclosed fluid passage;

heating said cleaning fluid around said orifice;

removing said cleaning fluid from said enclosed fluid passage;

determining if said clog has been removed from said particle counting system;

providing a rinse fluid;

drawing said rinse fluid into said enclosed fluid passage;

automatically flushing said rinse fluid through said enclosed fluid passage and through said orifice to dislodge said clog;

determining if said clog was dislodged by said flushing;

providing a cleaning fluid for removing said clog in said particle counting system;

automatically pumping said cleaning fluid through said orifice and said enclosed fluid passage;

removing said cleaning fluid from said enclosed fluid passage; and determining if said clog has been removed from said particle counting system.

2. A method of detecting leaks and clogs in a particle counting system for sensing and counting particles suspended in a sample fluid as said sample fluid is drawn through an orifice from a sample chamber to an enclosed fluid passage, comprising:

advancing said sample fluid from said sample chamber through said orifice to said enclosed fluid passage at a selected rate to maintain said enclosed fluid passage at a predetermined pressure level if said particle counting system is free of leaks and clogs;

sensing and counting particles suspended in said sample fluid as said sample fluid is drawn through said orifice from said sample chamber to said enclosed fluid passage;

sensing actual pressure in said enclosed fluid passage as said sample fluid is advanced through said orifice;

comparing said actual pressure level to said predetermined pressure level, wherein when said actual pressure level is less than said predetermined pressure level, a leak is detected, and wherein when said actual pressure level is greater than said predetermined pressure level, a clog is detected;

discontinuing the sensing and counting of particles suspended in said sample fluid if a leak is detected;

indicating that a leak exists in said particle counting system;

discontinuing said sensing and counting of particles suspended in said sample fluid when a clog is detected in said particle counting system;

providing a rinse fluid;

automatically flushing said rinse fluid through said enclosed fluid passage and said orifice to dislodge said clog when detected;

providing a cleaning fluid for removing said clog in said particle counting system;

automatically pumping said cleaning fluid through said orifice and said enclosed fluid passage;

removing said cleaning fluid from said enclosed fluid passage;

determining if said clog has been removed from said particle counting system.

providing a cleaning fluid for removing said clog in said particle counting system;

automatically pumping said cleaning fluid through said orifice and said enclosed fluid passage;

heating said cleaning fluid around said orifice;

removing said cleaning fluid from said enclosed fluid passage;

determining if said clog has been removed;

providing a rinse fluid;

drawing said rinse fluid into said enclosed fluid passage;

automatically flushing said rinse fluid through said enclosed fluid passage and through said orifice to dislodge said clog;

determining if the said clog was dislodged by said flushing;

providing a cleaning fluid for removing said clog in said particle counting system;

automatically pumping said cleaning fluid through said orifice and said enclosed fluid passage;

removing said cleaning fluid from said enclosed fluid passage; and determining if said clog has been removed from said particle counting system.

3. In a particle counting system for sensing and counting particles suspended in a sample fluid as said sample fluid is drawn through an orifice from a sample chamber to an enclosed fluid passage, the improvement comprising:

a pressure transducer coupled to said enclosed fluid passage for sensing actual pressure in said enclosed fluid passage;

a pump means, coupled to said enclosed fluid passage, for drawing said sample fluid through said orifice into said enclosed fluid passage at a selected rate to maintain said enclosed fluid passage at a predetermined pressure level if said orifice and enclosed fluid passage are unobstructed;

means, coupled to said transducer, for determining whether said actual pressure in said enclosed fluid passage is at an acceptable pressure level as said means for drawing advances said sample fluid through said orifice to said enclosed fluid passage, wherein an unacceptable pressure level indicates a clog impeding passage of fluid from said sample chamber through said aperture to said enclosed fluid passage;

means, coupled to said enclosed fluid passage, for automatically removing said clog when detected;

means, coupled to said enclosed fluid passage, for automatically flushing a rinse fluid through said enclosed fluid passage and said orifice to dislodge said clog;

means, coupled to said enclosed fluid passage, for automatically pumping a cleaning solution through said orifice and said enclosed fluid passage to remove said clog; and means, coupled to said enclosed fluid passage, for automatically testing to determine if said clog has been removed.

* * * * *